United States Patent [19]

Hwang

[11] 4,374,783

[45] Feb. 22, 1983

[54] O,O-DIALKYL-S-(2,3,4-TRICHLORO)BUTYL THIOPHOSPHATE

[76] Inventor: Seong T. Hwang, 6225 Garretson St., Burke, Va. 22015

[21] Appl. No.: 261,888

[22] Filed: May 8, 1981

[51] Int. Cl.[3] .............................................. C07F 9/165
[52] U.S. Cl. ..................................... 260/963; 568/24; 260/969
[58] Field of Search ......................................... 260/963

[56] References Cited

U.S. PATENT DOCUMENTS 3,980,738 9/1976 Arlt et al. ............................. 260/963

FOREIGN PATENT DOCUMENTS 50-35117 4/1975 Japan .

Primary Examiner—Anton H. Sutto

[57] ABSTRACT

The new compounds, O,O dialkyl S-(2,3,4 trihalo) butyl phosphorothioates, are prepared by reacting 2,3,4 trihalo-butyl sulfenyl chloride with O,O dialkyl hydrogen phosphites, or other salts. The compounds of this invention have pesticidal activity, especially insecticidal and nematocidal activity.

2 Claims, No Drawings

O,O-DIALKYL-S-(2,3,4-TRICHLORO)BUTYL THIOPHOSPHATE

DESCRIPTION OF THE INVENTION

This invention relates to new compounds having pesticidal activity. In particular, the present invention is concerned with compounds represented by

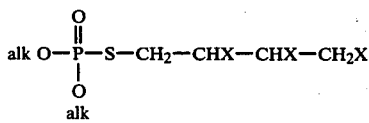

wherein alk is alkyl, and X is a halogen of atomic weight between 35 and 80, i.e., chlorine or bromine.

The compounds of the present invention can be prepared by reacting dialkyl hydrogen phosphites, or their salts, with 2,3,4 trihalo-butyl sulfenyl chloride. The reaction is conveniently carried out in an inert diluent such as hexane, carbon tetrachloride, chloroform, methylene chloride, alcohols, or other chlorinated solvents. The reaction occurs readily at room temperature. It is advantageous, however, to complete the reaction at slightly elevated temperatures.

2,3,4 trihalo butyl sulfenyl chlorides according to the invention are obtained by reacting bis(2,3,4 trihalobutyl) disulfide with chlorine at room temperature in the presence of an inert diluent such as carbon tetrachloride. In the case of dimethyl hydrogen phosphite and 2,3,4 trihalo-butyl sulfenyl chloride the reaction proceeds according to the following equation:

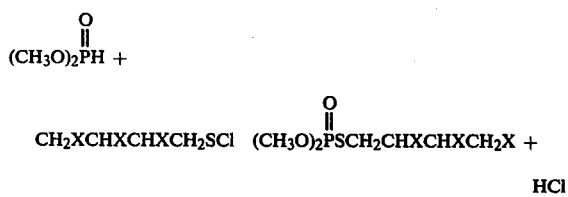

The 2,3,4 trichlorobutyl sulfenyl chloride employed is obtained by reacting bis(2,3,4 trichlorobutyl) disulfide with chlorine according to the invention. Many of the starting reactants employed in the process of this invention are available from commercial sources. The compounds obtained according to the invention are either non-distillable at atmospheric pressure, water insoluble oils, or solid substances.

The new compounds obtained in accordance with the invention have demonstrated broad-spectrum insecticidal and nematocidal activity; e.g. O,O-dimethyl S-(2,3,4 trichloro) butyl phosphorothioate kills aphids, flies, grasshoppers even in a concentration of 0.001 percent. The new compounds are, therefore, very valuable plant protecting agents.

The following examples are given by way of illustrations only for preparation of bis(2,3,4 trichlorobutyl) disulfide, the intermediate 2,3,4 trichlorobutyl sulfenyl chloride, and therefrom, the new compounds contemplated by the invention. These examples are not to be construed as limitations of this invention, since from such disclosure various changes and modifications which may fall within the scope and spirit thereof will become obvious to those skilled in the art.

EXAMPLE 1

To a mixture of 106.82 grams of 3,4-dichlorobutene-1 suspended with 2.94 grams of titanium tetrachloride were added 48.1 grams of sulfur monochloride at a temperature of 40°–45° C. over a period of one hour. The mixture was agitated for three hours at 60°–65° C., cooled to room temperature, and allowed to stand overnight. The excess amount of 3,4-dichlorobutene-1 was stripped off under vacuum. The material was diluted with 121 grams of carbon tetrachloride, and washed twice with 150 grams of water each time. Before separating the aqueous and organic layers, the mixture was filtered to remove titanium tetrachloride. The organic layer was dried and the solvent removed by vacuum stripping. Upon further stripping under a high vacuum there was obtained 119.6 grams of brownish-yellow oil of bis(2,3,4 trichlorobutyl) disulfide.

EXAMPLE 2

53.1 grams of bis(2,3,4 trichlorobutyl) disulfide prepared as in Example 1 were mixed with 17 grams of reaction solvent, carbon tetrachloride. To the mixture were introduced under continuous stirring 3 grams of chlorine gas over a two hour period at a temperature of 20°–25° C. which is maintained by external cooling by means of ice-water bath. The amount of chlorine used is 7 percent excess over the theoretical amount of chlorine required to convert the bis(2,3,4 trichlorobutyl) disulfide to 2,3,4 trichlorobutyl sulfenyl chloride. After stirring at 20°–25° C. for one hour and filteration the resulting mixture was subjected to vacuum distillation to remove the carbon tetrachloride solvent. The yield of 2,3,4 trichlorobutyl sulfenyl chloride as a yellow oil was 97.3 percent.

EXAMPLE 3

In a three necked 250 ml flask equipped with stirrer, addition funnel, thermometer, condenser, and a HCl absorption trap, 22.8 grams (0.1 gram mole) of 2,3,4 trichlorobutyl sulfenyl chloride prepared as in Example 2 were mixed with 45.6 grams of hexane. To this mixture were added 11.23 grams (2 percent excess over theoretical) of dimethyl hydrogen phosphite in the addition funnel over a period of one hour at 15°–20° C. This temperature was maintained by external cooling by means of cold water bath. After stirring for one hour at 15°–20° C. the reaction product was heated to 50° C. over a period of 50 minutes to drive off remaining HCl, and then allowed to cool to room temperature. 100 c.c. of water was added to the product which after agitation was filtered and allowed to separate layers. The solvent was removed from the organic layer by vacuum stripping. The final product contained 21.35 grams (70.8 percent yield) of O,O dimethyl S-(2,3,4 trichloro) butyl phosphorothioate in the form of a thick brown oil.

What is claimed is:

1. O,O dimethyl S-(2,3,4 trichloro) butyl phosphorothioate.

2. O,O diethyl S-(2,3,4 trichloro) butyl phosphorothioate.

* * * * *